US008225787B2

(12) United States Patent
Newman, Jr.

(10) Patent No.: US 8,225,787 B2
(45) Date of Patent: Jul. 24, 2012

(54) ADJUSTABLE PRESSURE DEVICE AND SYSTEM THEREOF

(75) Inventor: Lionel Newman, Jr., Los Angeles, CA (US)

(73) Assignee: Wet Nose Technologies, LLC, Los Angeles, CA (US)

( * ) Notice: Subject to any disclaimer, the term of this patent is extended or adjusted under 35 U.S.C. 154(b) by 737 days.

(21) Appl. No.: 12/365,809

(22) Filed: Feb. 4, 2009

(65) Prior Publication Data
US 2009/0194108 A1    Aug. 6, 2009

Related U.S. Application Data

(63) Continuation-in-part of application No. 11/849,259, filed on Aug. 31, 2007.

(51) Int. Cl.
*A61M 16/00* (2006.01)
(52) U.S. Cl. ......... 128/204.18; 128/202.27; 128/204.15; 128/205.27; 128/204.16
(58) Field of Classification Search ............ 128/204.18, 128/202.27, 204.15, 205.12, 205.27, 204.16
See application file for complete search history.

(56) References Cited

U.S. PATENT DOCUMENTS

| | | |
|---|---|---|
| 1,304,327 A | 5/1919 | Klay |
| 1,314,855 A | 9/1919 | Carpenter |
| 1,889,425 A | 11/1932 | Sorensen |
| 2,088,720 A | 8/1937 | Poliniak |
| 2,295,528 A | 9/1942 | Cutter et al. |
| 2,328,995 A | 9/1943 | Olds |
| 2,375,711 A | 5/1945 | Vondrak |
| 2,422,702 A | 6/1947 | Rodanet |
| 2,449,497 A | 9/1948 | McLeod |
| 2,812,765 A | 11/1957 | Tofflemire |
| 3,065,749 A | 11/1962 | Brass |
| 3,710,780 A | 1/1973 | Milch |
| 3,749,090 A | 7/1973 | Stewart |
| 3,804,089 A | 4/1974 | Bridgman |
| 3,827,433 A | 8/1974 | Shannon |
| 3,908,704 A | 9/1975 | Clement et al. |

(Continued)

FOREIGN PATENT DOCUMENTS
EP     0979660 A     2/2000
(Continued)

OTHER PUBLICATIONS

OA dated Apr. 6, 2009 for U.S. Appl. No. 11/849,268, 9 pages.

(Continued)

*Primary Examiner* — Clinton T Ostrup
(74) *Attorney, Agent, or Firm* — Turocy & Watson, LLP (57) ABSTRACT

An adjustable airway pressure system is provided. The system may include a cap and a canister. The cap may include a substantially hollow conduit having indicia indicative of a plurality of airway pressure values and adapted to receive and output exhaled gas. The conduit may have screw threads on an exterior surface of the conduit. The cap may also include an adjust collar circumscribing the conduit and having an interior surface with a second plurality of screw threads. The second plurality of screw threads may couple and be complementary to the first plurality of screw threads such that a rotation of the adjust collar causes the conduit to move in a substantially vertical direction. The conduit may be adapted to be adjusted to heights along a continuum. The canister may contain liquid and receive the conduit such that the received exhaled gas is output from the conduit into the liquid.

12 Claims, 9 Drawing Sheets

U.S. PATENT DOCUMENTS

| | | | |
|---|---|---|---|
| 3,949,749 A | 4/1976 | Stewart | |
| 3,972,326 A | 8/1976 | Brawn | |
| 4,080,989 A | 3/1978 | Chapelsky et al. | |
| 4,215,476 A | 8/1980 | Armstrong | |
| 4,299,221 A | 11/1981 | Phillips et al. | |
| 4,459,983 A | 7/1984 | Beyreuther et al. | |
| 4,464,316 A | 8/1984 | Michaels | |
| 4,468,216 A | 8/1984 | Muto | |
| 4,617,013 A | 10/1986 | Betz | |
| 4,634,420 A | 1/1987 | Spinosa et al. | |
| 4,857,047 A | 8/1989 | Amoils | |
| 5,167,622 A | 12/1992 | Muto | |
| 5,255,675 A | 10/1993 | Kolobow | |
| 5,263,934 A | 11/1993 | Haak | |
| 5,269,296 A | 12/1993 | Landis | |
| D358,475 S | 5/1995 | Choksi et al. | |
| 5,477,852 A | 12/1995 | Landis et al. | |
| 5,557,049 A | 9/1996 | Ratner | |
| 5,575,774 A | 11/1996 | Chen | |
| 5,626,565 A | 5/1997 | Landis et al. | |
| 5,653,231 A | 8/1997 | Bell | |
| 5,687,715 A | 11/1997 | Landis et al. | |
| 5,730,727 A | 3/1998 | Russo | |
| 5,803,310 A * | 9/1998 | Soon | 222/1 |
| D410,021 S | 5/1999 | Heyman et al. | |
| 5,899,878 A | 5/1999 | Glassman | |
| 6,041,777 A | 3/2000 | Faithfull et al. | |
| 6,045,516 A | 4/2000 | Phelan | |
| 6,050,263 A | 4/2000 | Choksi et al. | |
| 6,149,622 A | 11/2000 | Marie | |
| D439,973 S | 4/2001 | Choksi | |
| 6,284,222 B1 | 9/2001 | Driehuys | |
| D449,378 S | 10/2001 | Rogone et al. | |
| 6,494,203 B1 | 12/2002 | Palmer | |
| 6,520,021 B1 | 2/2003 | Wixey et al. | |
| D474,269 S | 5/2003 | Choksi et al. | |
| 6,576,191 B1 | 6/2003 | Myrick et al. | |
| 6,770,050 B2 | 8/2004 | Epstein | |
| 6,795,722 B2 | 9/2004 | Sheraton et al. | |
| 6,805,120 B1 | 10/2004 | Jeffrey et al. | |
| 6,805,129 B1 | 10/2004 | Pless et al. | |
| D506,547 S | 6/2005 | Cruz et al. | |
| 6,958,050 B1 | 10/2005 | Choski et al. | |
| 7,066,917 B2 | 6/2006 | Talamonti | |
| 7,077,154 B2 | 7/2006 | Jacobs et al. | |
| 7,185,681 B2 | 3/2007 | Romano | |
| 7,195,018 B1 * | 3/2007 | Goldstein | 128/207.18 |
| D590,056 S | 4/2009 | McCrary et al. | |
| 7,601,001 B1 | 10/2009 | McCrary et al. | |
| 2001/0044599 A1 | 11/2001 | Lo | |
| 2002/0108614 A1 | 8/2002 | Schultz | |
| 2003/0047185 A1 | 3/2003 | Olsen et al. | |
| 2003/0065263 A1 | 4/2003 | Hare et al. | |
| 2003/0069553 A1 | 4/2003 | Talamonti | |
| 2004/0065330 A1 | 4/2004 | Landis | |
| 2004/0118733 A1 | 6/2004 | Pauli | |
| 2004/0244804 A1 | 12/2004 | Olsen et al. | |
| 2005/0049547 A1 | 3/2005 | Anspach et al. | |
| 2005/0072470 A1 | 4/2005 | Jacobs et al. | |
| 2005/0150505 A1 | 7/2005 | Burrow et al. | |
| 2005/0182353 A1 | 8/2005 | Schmidberger et al. | |
| 2005/0256462 A1 | 11/2005 | Underwood | |
| 2005/0277898 A1 | 12/2005 | Dimalanta et al. | |
| 2006/0079832 A1 | 4/2006 | Akahoshi | |
| 2006/0229632 A1 | 10/2006 | Madden et al. | |
| 2007/0078378 A1 | 4/2007 | Kao et al. | |
| 2007/0107737 A1 | 5/2007 | Landis et al. | |
| 2007/0175473 A1 | 8/2007 | Lewis et al. | |
| 2007/0191783 A1 | 8/2007 | Shaw et al. | |

FOREIGN PATENT DOCUMENTS

| | | |
|---|---|---|
| EP | 1084727 | 4/2006 |
| WO | 98/58694 A | 12/1998 |
| WO | 01/64272 A | 9/2001 |
| WO | 2004/033007 A1 | 4/2004 |
| WO | WO2005056091 A1 | 6/2005 |
| WO | 2009/029702 A1 | 3/2009 |

OTHER PUBLICATIONS

International Search Report mailed Nov. 6, 2008 for International Application No. PCT/US20081074748, 2 pages.

International Search Report mailed Nov. 6, 2008 for International Application No. PCT/US2008/074574, 2 pages.

OA dated Sep. 29, 2009 for U.S. Appl. No. 11/849,268, 19 pages.

International Search Report mailed Nov. 2, 2004 for International Application No. PCT/IB2003/04419, 2 pages.

OA dated Jan. 13, 2010 for U.S. Appl. No. 11/849,268, 34 pages.

Written Opinion of the International Searching Authority mailed Nov. 6, 2008 for PCT Application No. PCT/US2008/074574, 35 pages.

Frischer, et al. Eosinophil-derived proteins in nasal lavage fluid of neonates of allergic parents and the development of respiratory symptoms during the first 6 months of life. Allergy 2000: 55: 773-777, ISSN 0105-4538. http://onlinelibrary.wiley.com/doi/10.1034/j.1398-9995.2000.00773.x/pdf. Last accessed Oct. 6, 2010, 5 pages.

Waisman. Non-Traumatic Nasopharyngeal Suction in Premature Newborn Infants with Upper Airway Obstruction from Secretions Following Nasal CPAP. J Pediatr 2006;149:279. http://download.journals.elsevierhealth.com/pdfs/journals/0022-3476/PIIS002234760600148X.pdf. Last accessed Oct. 6, 2010, 1 page.

Okada, et al. Pressure-Controlled Dual Irrigation-Suction System for Microneurosurgery: Technical Note. www.neurosurgery-online.com, E625, vol. 65, No. 3, Sep. 2009. http://pt.wkhealth.com/pt/re/mercldpdfhandler.00006123-200909000-00032.pdf;jsessionid=MsvLyq9Y7c928drTcGsSkYzDJy61CfX4zbyC66q6kcxL5Ghd RLKy!1137524313!181195628!8091!-1. Last accessed Oct. 6, 2010, 4 pages.

Vain, et al. Oropharyngeal and nasopharyngeal suctioning of meconium-stained neonates before delivery of their shoulders: multicenter, randomized controlled trial (Abstract), The American College of Obstetricians and Gynecologists, vol. 104, No. 5, Part 1, Nov. 2004.

Garzon, et al. Management of Respiratory Syncytial Virus With Lower Respiratory Tract Infection in Infants and Children. AACN Clinical Issues, vol. 13, No. 3, Aug. 2002, pp. 421-430.

Balfour-Lynn, et al. Nasal IgA response in wheezy infants. Archives of Disease in Childhood 1993; 68: 472-476. Last accessed Oct. 18, 2010, 5 pages.

Celik, et al. A Current Conflict: Use of Isotonic Sodium Chloride Solution on Endotracheal Suctioning in Critically Ill Patients. Dimens Crit Care Nurs. 2006;25(1):11/14. http://www.nursingcenter.com/pdf.asp?AID=630764. Last accessed Oct. 18, 2010, 4 pages.

Stokowski (Section Editor). Endotracheal Suctioning Increases Cerebral Blood Flow in the Very Low Birth-Weight Infant, Advances in Neonatal Care: Apr. 2008—vol. 8—Issue 2—pp. 75-77. doi: 10.1097101. Anc.0000317254.30460.5d, Noteworthy Professional News, downloaded Mar. 24, 2008, 3 pages.

Virolainen, et al. New Method to Assess Dilution of Secretions for Immunological and Microbiological Assays. Journal of Clinical Microbiology, May 1993, p. 1382-1384, vol. 31, No. 5. http://jcm.asm.org/cgi/reprint/31/5/1382. Last accessed Oct. 19, 2010, 3 pages.

Heikkinen, et al. Quantification of Cytokines and Inflammatory Mediators in Samples of Nasopharyngeal Secretions with Unknown Dilution. Pediatric Research: Feb. 1999—vol. 45—Issue 2—pp. 230-234. http://journals.lww.com/pedresearch/Fulltext/1999/02000/Quantification_of_Cytokines_and_Inflammatory.12.aspx#. Last accessed Oct. 19, 2010, 9 pages.

Foglia, et al. Ventilator-Associated Pneumonia in Neonatal and Pediatric Intensive Care Unit Patients. Clinical Microbiology Reviews, vol. 20, No. 3, Jul. 2007, p. 409-425. http://cnnr.asm.org/cgi/reprint/20/3/409.pdf. Last accessed Oct. 19, 2010, 17 pages.

Kaiser, et al. Tracheal suctioning is associated with prolonged disturbances of cerebral hemodynamics in very low birth weight infants. Journal of Perinatology (2008) 28, 34-41, published online, Oct. 25, 2007. http://www.umanitoba.ca/faculties/medicine/units/pediatrics/sections/neonatology/media/Oct20-08.pdf. Last accessed Oct. 19, 2010, 8 pages.

Folk. Guide to Capillary Heelstick Blood Sampling in Infants. Advances in Neonatal Care • vol. 7, No. 4 • pp. 171-178. http://www.nursingcenter.conn/pdf.asp?AID=735611. Last accessed Oct. 19, 2010, 8 pages.

Lasocki, et al. Open and Closed-circuit Endotracheal Suctioning in Acute Lung Injury: Efficiency and Effects on Gas Exchange. Anesthesiology: Jan. 2006—vol. 104—Issue 1—pp. 39-47, Clinical Investigations. http://journals.lww.com/anesthesiology/Fulltext/2006/01000/Open_and_Closed_circuit_Endotracheal_Suctioning_in.8.aspx. Last accessed Oct. 19, 2010, 9 pages.

Lanter. Clinical Research and the Development of New Devices: Considerations for Nurses. Dimensions of Critical Care Nursing: May/Jun. 2007—vol. 26—Issue 3—pp. 117-120. http://journals.1ww.com/dccnjournal/Fulltext/2007/05000/Clinical_Research_and_the_Development_of_New.7.aspx. Last accessed Oct. 19, 2010, 4 pages.

National Nosocomial Infections Surveillance (NNIS) System Report, data summary from Jan. 1992 through Jun. 2004, issued Oct. 2004. http://www.cdc.gov/ncidod/dhqp/pdf/nnis/2004NNISreport.pdf. Last accessed Oct. 19, 2010, 16 pages.

Ingram, et al. Eosinophil Cationic Protein in Serum and Nasal Washes from Wheezing Infants and Children. Journal of Pediatrics, vol. 127, issue 4, Oct. 1995. Retrieved from the internet on Nov. 10, 2010, 11 pages.

Heikkenen, et al. Free Secretory Component as a Standardization Protein for Nasopharyngeal Specimens from Children with Upper Upper Respiratory Tract Infection. Acta Paediatr 88: 150-153, 1999.

Bonner, et al. The Nursing Care of the Infant Receiving Bubble CPAP Therapy. Advances in Neonatal Care • vol. 8, No. 2 • pp. 78-95. Last accessed Nov. 13, 2010, 18 pages.

Klimek, et al. Norm Values for Eosinophil Cationic Protein in Nasal Secretions: Influence of Specimen Collection. Clinical and Experimental Allergy, 1999, vol. 29, pp. 367-374.

Norris, et al. Nursing Procedures and Alterations in Transcutaneous Oxygen Tension in Premature Infants. Nursing Research, vol. 31, No. 6, Nov./Dec. 1982, pp. 330-336.

Samolinski, et al. Changes in Nasal Cavity Dimensions in Children and Adults by Gender and Age. Laryngoscope, 117:1429-1433, Aug. 2007, The American Laryngological, Rhinological and Otological Society, Inc.

Weinstein, et al. Recommendations of the Panel on Cost-Effectiveness in Health and Medicine. JAMA, Oct. 16, 1996—vol. 276, No. 15, 6 pages.

Fisher & Paykel Healthcare Product Catalog copyright 2004, 16 pages.

Fisher & Paykel Healthcare Annual Report 2002, 32 pages.

Petry, Fisher & Paykel 510(k) Summary of Safety and Effectiveness Information, 6 pages, Apr. 3, 2003.

http://www.fphcare.com/rsc.html, last accessed Apr. 26, 2010, 1 page.

http://www.fphcare.com/rsc/infant-care/resuscitation.html, last accessed Apr. 26, 2010, 1 page.

http://www.fphcare.com/rsdinfant-care/non-invasive-ventilation.html, last accessed Apr. 26, 2010, 1 page.

http://www.fphcare.com/rsdrac-clinical-and-applications/infant-ca/why-bubble-cpap-is-vital.html, last accessed Apr. 26, 2010, 2 pages.

http://www.fphcare.com/product-overview/chambers/humidification-chambers/mr290-autofeed.html, last accessed Apr. 26, 2010, 1 page.

http://www.fphcare.com/product-overview/chambers/humidification-chambers/mr210-mr250-chamber.html, last accessed Apr. 26, 2010, 1 page.

http://www.fphcare.com/product-overview/chambers/humidification-chambers/mr225-manual-feed.html, last accessed Apr. 26, 2010, 1 page.

http://www.fphcare.com/osa/cpap-solutions/cpap/sleepstyle-200.html, last accessed Apr. 26, 2010, 2 pages.

http://www.fphcare.com/osa/cpap-solutions/cpap/sleepstyle-240.html, last accessed Apr. 26, 2010, 2 pages.

http://www.fphcare.com/osa/cpap-solutions/cpap/sleepstyle-600.html, last accessed Apr. 26, 2010, 2 pages.

http://www.fphcare.com/osa/cpap-solutions/autocpap/sleepstyle-250.html, last accessed Apr. 26, 2010, 2 pages.

Babi.Plus™ Bubble Pap Valve 0—10 cm H2O, Safe, accurate method to deliver CPAP therapy in neonatal critical care environments, 2010, 1 page.

B&B Medical Technologies, Babi.Plus™ Bubble Pap Valve 0—10 cm H2O, 2005, 2 pages.

B&B Medical Technologies, Babi.Plus™ Bubble Pap Valve 0—10 cm H2O gives clinicians a safe, accurate, convenient method to deliver Cpap therapy for neonates and premature infants, 1 page, Mar. 19, 2010.

Airways Development LLC, Waterseal Canister & Accessories, Aug. 2004, 1 page.

A Plus Medical 510(k) Summary, 5 pages, May 20, 2009.

Presentation Jul. 2007, 16 pages.

http://www.airwaysdevelopment.com/product.asp, last accessed Apr. 28, 2010, 1 page.

OA dated May 28, 2010 for U.S. Appl. No. 11/849,268, 39 pages.

OA dated Oct. 28, 2011 for U.S. Appl. No. 11/849,259, 71 pages.

* cited by examiner

ADJUSTABLE PRESSURE DEVICE AND SYSTEM THEREOF

CROSS REFERENCE TO RELATED APPLICATIONS

This continuation-in-part application claims priority to and the benefit of U.S. patent application Ser. No. 11/849,259, filed Aug. 31, 2007 and titled "Exhalatory Pressure Device and System Thereof," the entire contents of which are incorporated herein by reference.

FIELD OF THE INVENTION

The present invention relates to bubble nasal continuous positive airway pressure ("BNCPAP") systems, in general, and to apparatus for regulating airway pressure in BNCPAP systems, in particular.

BACKGROUND

BNCPAP systems are used to treat a wide range of patients, including, but not limited to, neonates and premature babies, infants, children, adults, geriatrics and animals. Conventional BNCPAP systems include a pressure device having a canister of liquid into which exhalatory gases from a patient may be provided. The gases are transmitted into the liquid via a conduit, and the patient advantageously experiences airway pressure, which is backpressure that is felt in the patient's lungs as a result of exhaling into the liquid. The airway pressure may aid in lung tissue development and other improvements. The quantity of the airway pressure depends on the depth of the conduit in the liquid and the amount of liquid in the pressure device. Accordingly, unstable, movable conduits that shift may result in an undesirable and potentially dangerous shift in pressure experienced by the patient. Conventional pressure devices include a canister having a very flexible lid with an aperture formed through the lid into which the conduit may be positioned. These devices disadvantageously allow the aforementioned movement and corresponding shift in pressure. Accordingly, it may be desirable to have one or more embodiments of a BNCPAP pressure device disposed to provide a substantially stable airway pressure into which a patient must exhale. Additionally, to increase the accuracy of the airway pressure that the patient experiences, it may be desirable to have one or more embodiments of a BNCPAP pressure device that may be adjusted to provide airway pressure at any value on a continuum between a maximum pressure and a minimum pressure.

Additionally, after extended usage, the liquid in the column may evaporate and/or splash out of the column, thereby requiring regular replacement of liquid. However, the removal of the lid on the canister may allow bacteria to enter the canister, and patient infection may result. Accordingly, it may be desirable to have one or more embodiments of a BNCPAP pressure device that includes a pre-filled liquid canister into which the patient exhales.

SUMMARY OF EMBODIMENTS OF THE INVENTION

In one embodiment, an adjustable airway pressure system may be provided. The system may include a cap and a canister. The cap may include a substantially hollow conduit having indicia indicative of a plurality of airway pressure values and adapted to receive and output exhaled gas. The conduit may have screw threads on an exterior surface of the conduit. The cap may also include an adjust collar circumscribing the conduit and having an interior surface with a second plurality of screw threads. The second plurality of screw threads may couple and be complementary to the first plurality of screw threads such that a rotation of the adjust collar causes the conduit to move in a substantially vertical direction. The conduit may be adapted to be adjusted to heights along a continuum. The canister may contain liquid and receive the conduit such that the received exhaled gas is output from the conduit into the liquid.

BRIEF DESCRIPTION OF THE FIGURES

Purposes and scope of the exemplary embodiments described below will be apparent from the following detailed description in conjunction with the appended figures in which like reference characters are used to indicate like elements, and in which.

DETAILED DESCRIPTION OF EMBODIMENTS OF THE INVENTION

Figure 1:
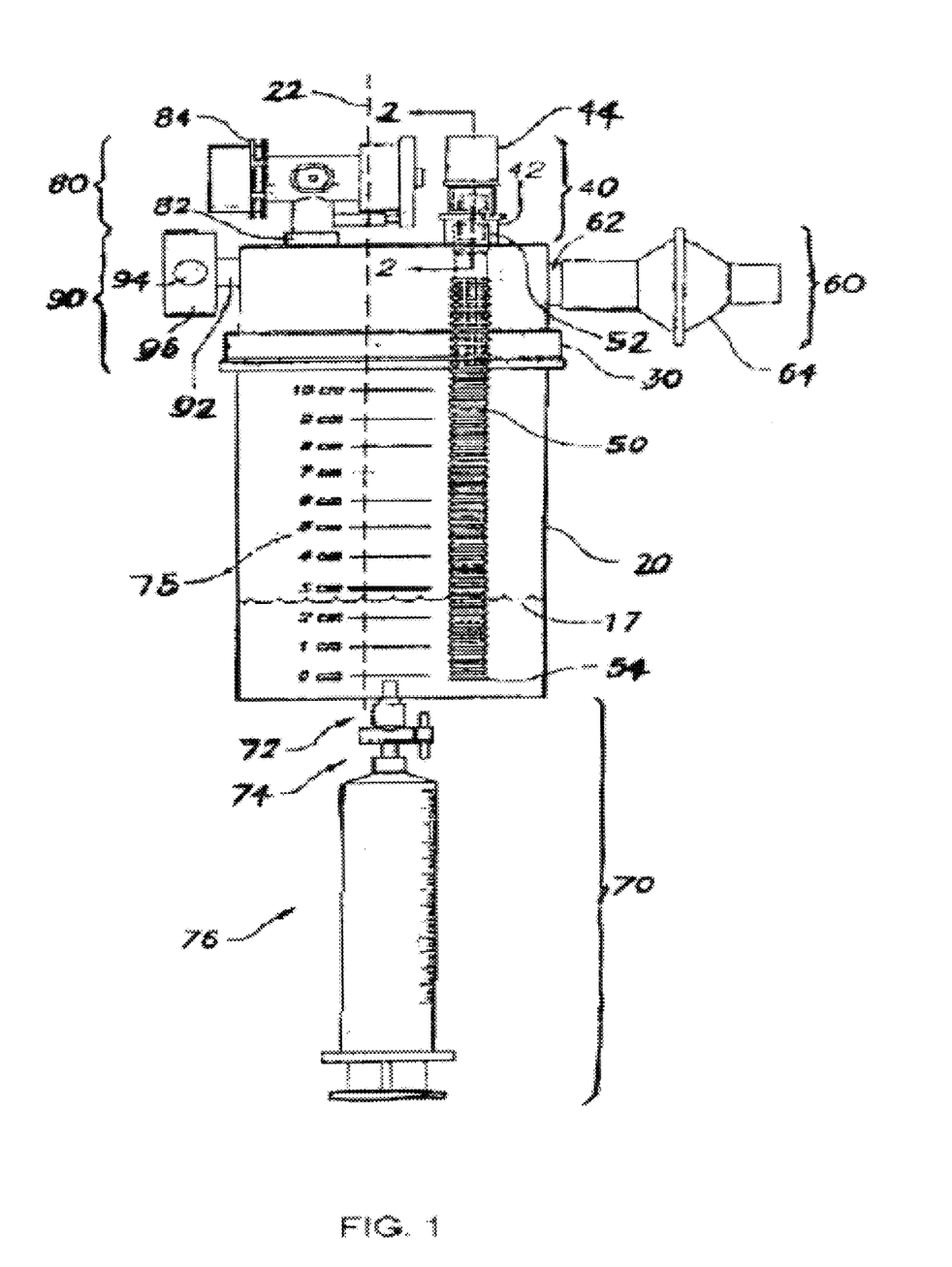
FIG. 1 is a side view of a pressure device according to an embodiment of the present invention.

FIG. 1 is a side view of a pressure device according to an embodiment of the present invention. The pressure device 10 may be disposed to provide pressure into which a patient must exhale. In some embodiments, the pressure device 10 may be used by caregivers to provide BNCPAP care to patients of any age, including, but not limited to, neonates, premature babies, infants, children, adults and/or geriatrics. In some embodiments, the pressure device 10 may also be used by caregivers to provide BNCPAP care to animals.

In one embodiment, the pressure device 10 may include a canister 20, a lid 30, an adapter 42 and a substantially immovable conduit 50. In some embodiments, the pressure device 10 may also include one or more of the following: an expiratory tube 44 of an adapter subsystem 40, a filtering subsystem 60, a liquid level adjustment subsystem 70, a pressure measurement subsystem 80 and/or a structure support subsystem 90. One or more of the components of the pressure device 10 may be coupled together and/or integrally formed with one another. In some embodiments, the pressure device 10 may include substantially rigid components and/or be less than one pound in weight.

The canister 20 may be formed of a substantially rigid material. In some embodiments, the canister 20 may be formed of a material allowing a caregiver to view a level of a liquid 17 in the canister 20. The canister 20 may be generally vertical and aligned with axis 22 during use of the pressure device 10. The exterior surface of the top portion of the canister 20 may include grooves or may be smooth for receiving a lid 30 over a mouth of the canister 20.

The canister 20 may be disposed to hold liquid 17. In some embodiments, the liquid 17 may be a solution including water and/or acetic acid. In some embodiments, the solution may be approximately 25% acetic acid. In some embodiments, the liquid 17 may be vinegar, which may reduce the growth of microorganisms known as pseudomonas.

In various embodiments, indicia 15 may be permanently or temporarily affixed to the canister 20 through any suitable methods including, but not limited to, being printed in or on the canister 20 or applied to a surface of the canister 20 using an indicator strip (not shown) having indicia 15 thereon. The indicia 15 may represent the airway pressure against which the patient must exhale. In some embodiments, the indicia 15 are a plurality of values in descending order from a top portion of the canister 20 to a bottom portion of the canister 20 as shown in FIG. 1. In some embodiments, the lowest value may be zero. In some embodiments, the indicia 15 may be presented in centimeters and represent centimeters of water pressure, i.e., cm $H_2O$.

Accordingly, in these embodiments, a caregiver may conveniently determine the airway pressure that a patient may experience by determining the height of the liquid 17 in the canister 20 using the indicia 15. Using the indicia 15 to determine the pressure may prevent the need to perform mathematical calculations to determine the pressure and may thereby reduce errors by caregivers.

In one embodiment, the diameter of canister 20 may be 7.5 cm and the height of the indicia 15 from the top to the bottom portion of the canister 20 may be 10 cm. The levels of the liquid 17 may calibrated in one cm increments from 0 to 10 cm, which may correspond to 0 to 10 cm $H_2O$ airway pressure. In embodiments wherein the pressure device 10 includes a pressure gauge (not shown) on a top portion of the canister 20, the total height of the canister 20 may be between 18 and 22 cm.

In some embodiments, the pressure device 10 may also include a liquid level adjustment subsystem 70 operably coupled to the canister 20. The canister 20 may have a first inlet (not shown) into which an attachment mechanism 72 of the liquid level adjustment subsystem 70 may be received. The attachment mechanism 72 may be disposed to be coupled to fluid flow mechanism 74, which may be disposed to stop or reduce the flow of liquid 17 from the canister 20. In some embodiments, the fluid flow mechanism 74 may be a stop cock. In some embodiments, the stop cock may be a luer-lock stop cock. In some embodiments, the luer-lock stop cock connection may be a connection point for a syringe. In some embodiments, the syringe may be a 30 to 60 cm syringe. Accordingly, the liquid level adjustment subsystem 70 may provide for fairly precise adjustments of the level of the liquid 17 and, correspondingly, the airway pressure into which the patient must exhale. In various embodiments, any suitable mechanism for stopping or reducing the flow of liquid 17 may be used.

The lid 30 may be disposed to be coupled to and to substantially cover a mouth portion of the canister 20. The lid 30 may be coupled to the outside of the canister 20 (as shown in FIG. 1) or to the inside of the canister 20 (not shown). The lid 30 may be coupled to the mouth portion of the canister 20 by any suitable method. In some embodiments, ridges on the interior surface of the lid 30 meet with grooves on the surface canister 20 to provide a screw-on lid. In some embodiments, a smooth interior surface of the lid 30 meets with a smooth surface of the canister 20 and the lid 30 may be telescopically coupled to the inside or outside of the canister 20.

The lid 30 may be composed of a rigid material. In some embodiments, the lid 30 may be composed of hardened plastic, hardened glass or another rigid material. In various embodiments, the rigidity of the lid 30 may be such that the lid 30 maintains a substantially undeformed shape during insertion of snugly-fitting components into inlets (not shown) in the lid 30 and during the use of the pressure device 10. The lid 30 may be any suitable shape for substantially covering a mouth portion of the canister 20.

Figure 2:
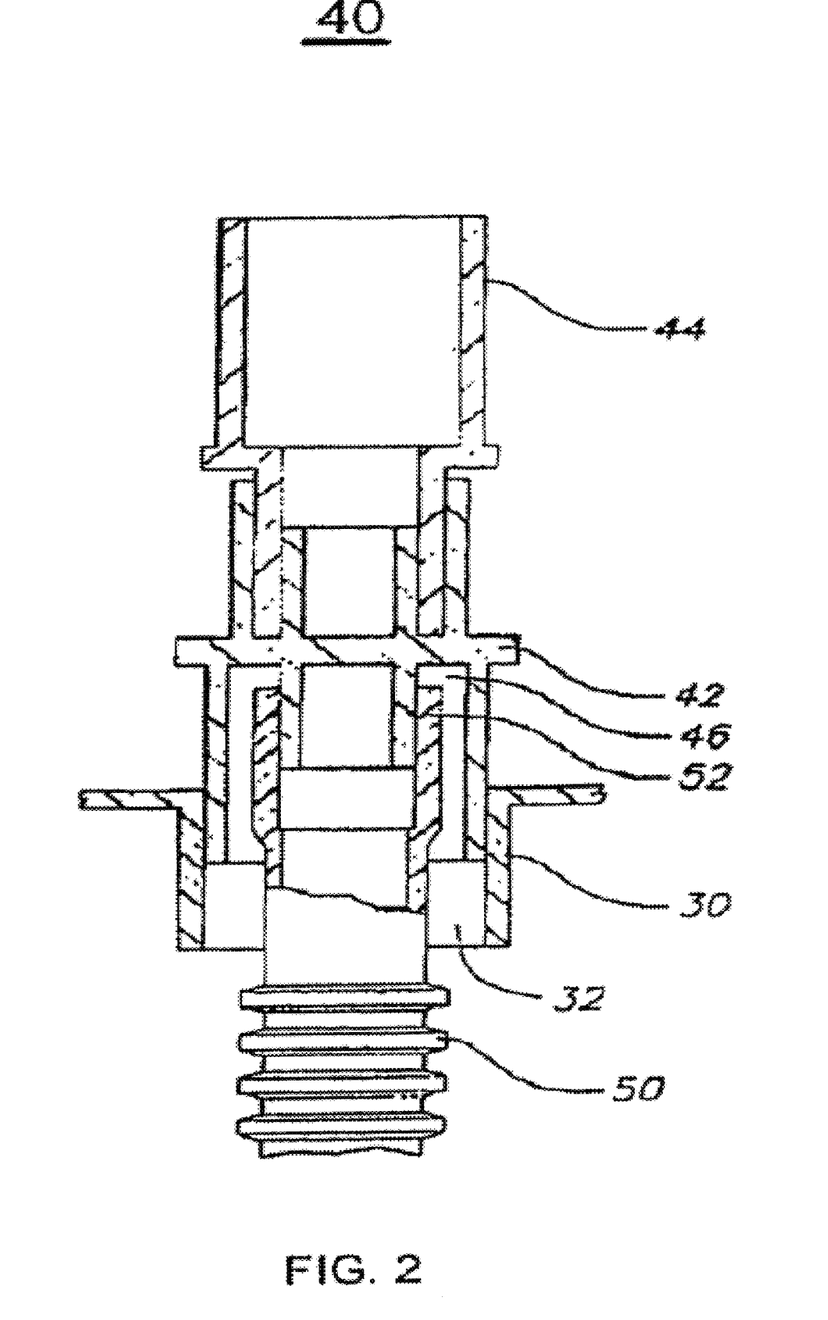
FIG. 2 is an embodiment of a cross-sectional view taken along line 2-2 of the adapter subsystem of the pressure device of FIG. 1 according to an embodiment of the present invention.

FIG. 2 is an embodiment of a cross-sectional view taken along line 2-2 of the adapter subsystem of the pressure device of FIG. 1 according to an embodiment of the present invention. With reference to FIGS. 1 and 2, the lid 30 may include an adapter inlet 32 located in the lid 30. The adapter inlet 32 may be dimensioned to snugly receive and retain an adapter 42, which may be positioned in the adapter inlet 32. In some embodiments, the adapter 42 may be snugly positioned in the adapter inlet 32 forming a substantially tight seal.

The adapter 42 may be disposed to retain a first end 52 of a substantially immovable conduit 50. In some embodiments, the adapter 42 simply receives and retains the first end 52. In some embodiments, the adapter 42 may be disposed to retain the conduit 50 such that the conduit 50 may be substantially immovable relative to the axis 22 of the canister 20. In some embodiments, the adapter 42 may include one or more recesses 46 for slidably receiving the first end 52 of the substantially immovable conduit 50. In some embodiments, the adapter 42 may be disposed with any suitable structure for snugly receiving and retaining the first end 52 of the substantially immovable conduit 50 in a substantially immovable position. In some embodiments, the adapter subsystem 40 may include an expiratory tube 44 coupled to the adapter 42. In some embodiments, the expiratory tube 44 and adapter 42 may form a seal that may be substantially airtight or that allows only a negligible amount of gas exhaled by the patient to be released through the seal.

In some embodiments, the expiratory tube 44 may have a first end that is a 22 millimeter (mm) female adapter connector. Accordingly, in some embodiments, the expiratory tube 44 may be coupled to the canister 20 and/or the adapter 42 without additional connectors or extensions. In some embodiments, the pressure device 10 may include an expiratory tube connector (not shown) adapted to couple the expiratory tube 44 to the canister 20 and/or to the adapter 42.

Figure 4:
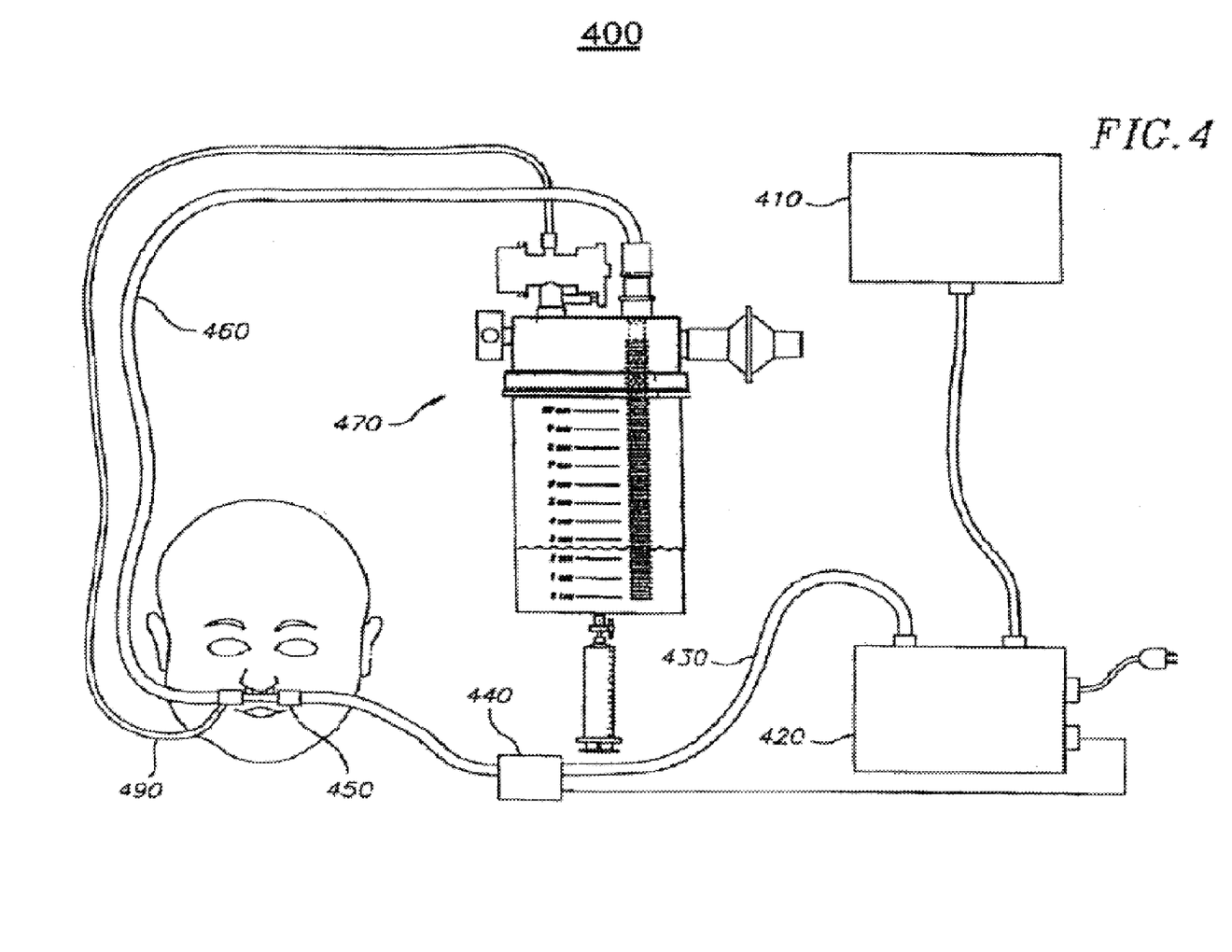
FIG. 4 is an illustration of a BNCPAP system having the pressure device of FIG. 1 according to an embodiment of the present invention.

FIG. 4 is an illustration of a BNCPAP system having the pressure device of FIG. 1 according to an embodiment of the present invention. Referring to FIGS. 1, 2 and/or 4, although the embodiments show the adapter 42 and the expiratory tube 44 as two separate components, the pressure device 10 may include a single adapter mechanism (not shown) having a first end and a second end wherein the first end may be disposed to couple to the conduit 50 and the second end may be disposed to couple to the expiratory tube 44.

The conduit 50 may be composed of semi-rigid material. In some embodiments, the conduit 50 may be composed of hardened plastic. In various embodiments, the conduit 50 may be a corrugated tube (as shown in FIG. 1) or a tube having a smooth exterior surface. In some embodiments, the conduit 50 may be a substantially immovable, corrugated tube. In various embodiments, the length of the conduit 50 may be substantially vertical and therefore parallel to the axis 22, as shown with reference to FIG. 1. In some embodiments, the conduit 50 may be L-shaped with a substantially vertical portion of the L-shape provided in the portion of the canister 20 in which the liquid 17 may be provided.

The conduit 50 may be any number of diameters allowing the conduit 50 to be snugly retained by the adapter 42. In some embodiments, the diameter of the conduit 50 may be 10 or 15 mm and corrugated. The adapter 42 and/or the canister 20 may be adapted to couple to 10 and 15 mm corrugated conduits. The conduit 50 may be coupled to the interior of the adapter 42 as shown in FIG. 1 or to the exterior of the adapter 42 (not shown).

In various embodiments, the length of the conduit 50 may be such that when the adapter 42 may be positioned in the adapter inlet 32 and the first end 52 of the conduit 50 may be coupled to the adapter 42, a second end 54 of the conduit 50 may be aligned with the indicia 15 corresponding to the smallest value in the descending order of indicia 15. In some embodiments, the second end 54 of the conduit 50 may be substantially aligned with the indicia 15 corresponding to zero cm $H_2O$ (as shown in FIG. 1). In some embodiments, the second end 54 of the conduit 50 may be positioned within + or −0.25 cm of the indicia 15 indicative of zero cm $H_2O$ pressure.

In various embodiments, the airway pressure may be proportional to the depth of the second end 54 of the conduit 50 below the surface of the liquid 17. By way of example, but not limitation, the second end 54 of the conduit 50 may be positioned at the indicia equal to 5 cm, which may cause the patient to experience an airway pressure of 5 cm $H_2O$.

In some embodiments, the conduit 50 may be substantially immovable after being positioned in the canister 20. In some embodiments, the conduit 50 may be substantially immovable relative to the axis 22 of the canister 20 such that the second end 54 of the conduit 50 may be maintained at substantially a same height corresponding to a substantially same value of the indicia 15 before and while the pressure device 10 may be in use. The pressure device 10 may be in use when the liquid 17 may be provided in the canister 20, and an exhalatory gas may be received in the liquid 17 via the conduit 50. In some embodiments, the second end 54 of the conduit 50 may be substantially immovable relative to the axis 22 of the canister 20 such that the second end 54 of the conduit 50 does not move more than 1 cm relative to the axis 22 of the canister 20.

Referring back to FIG. 1, in some embodiments, the lid 30 may also include a filter inlet (not shown) for providing a filtering subsystem 60 as part of the pressure device 10. The filtering subsystem 60 may include an air filter adapter 62 attached to the filter inlet and coupleable to an air filter 64. In some embodiments, the filter inlet may be provided in the canister 20 and the filtering subsystem 60 may be provided as part of the pressure device 10 by being coupled to the canister 20.

The air filter adapter 62 and the air filter 64 may each have channels (not shown) formed therethrough. The channels may be in fluid communication with one another such that gases associated with the liquid 17 in the canister 20 may travel from the canister 20 through the air filter adapter 62 and into the air filter 64. In some embodiments, the air filter 64 may be composed of material adapted to filter odors in the gases associated with the liquid 17.

In some embodiments, the lid 30 may also provide a pressure measurement subsystem 80. The lid 30 may provide the pressure measurement subsystem 80 by having a pressure subsystem inlet (not shown) into which the pressure gauge attachment 82 may be received, or the pressure measurement subsystem 80 may be coupled to any exterior surface of the lid 30. In some embodiments, the pressure measurement subsystem 80 may be coupled to any exterior surface of the canister 20. In some embodiments, the pressure measurement subsystem 80 may not be coupled to the lid 30 or the canister 20.

The pressure gauge attachment 82 may be coupled to a pressure gauge 84. In some embodiments, the pressure gauge 84 may be calibrated in cm $H_2O$ pressure values. In some embodiments, the pressure gauge 84 may be a disposable pressure gauge. The pressure gauge 84 may be discarded after a single patient's use. In some embodiments, the pressure gauge 84 may be a spring-loaded disposable pressure gauge.

The pressure gauge 84 may be disposed to measure proximal airway pressure output from and/or near the respiratory body cavity of the patient. In some embodiments, the respiratory body cavity may be the nose and/or the mouth. In some embodiments, a connector (not shown) may connect a tube to the pressure gauge 84.

In some embodiments, the lid 30 may also provide a structure support subsystem 90. The lid 30 may provide the structure support subsystem 90 by having a support subsystem inlet (not shown) into which a structure support subsystem 90 may be received, or the structure support subsystem 90 may be coupled to any exterior surface of the lid 30. In some embodiments, the subsystem 90 may be coupled to any exterior surface of the canister 20.

In some embodiments, the structure support subsystem 90 may include a bracket 96 disposed to couple to a support structure for mounting the pressure device 10. In various embodiments, the support structure may be a rail, a pole or any other structure on which the pressure device 10 may be supported. The orientation of the support structure may be substantially parallel to or perpendicular to the axis 22 of the canister 20 or in any other orientation relative to the axis 22 of the canister 20 while maintaining the lid 30 and canister 20 in a substantially upright position.

In some embodiments, the bracket 96 may be adapted to swivel or otherwise shift in orientation. The bracket 96 may be swivelable to be mounted to a support mechanism having an orientation that may be substantially parallel to, substantially perpendicular to or having another orientation relative to the axis 22 of the canister 20 while maintaining the lid 30 and canister 20 in a substantially upright position. The structure support subsystem 90 may include a swivel portion 92 coupled to a bracket 96 via a mechanism 94 for coupling the swivel portion 92 to the bracket 96. In some embodiments, the swivel portion 92 may be a swivel connector. In some embodiments, the mechanism 94 may be a thumb knob bracket mounting screw. In some embodiments, the bracket 96 may be a pole-rail mounting bracket. In some embodiments, the thumb knob bracket mounting screw 94 may be turned and tightened to secure the bracket 96 onto a support structure. The screw 94 may be used to securely lock the bracket 96 to the support structure. In some embodiments, one or more of the bracket 96, swivel portion 92 or the mechanism 94 may be rigid and/or composed of hardened plastic. Accordingly, in various embodiments, the pressure device 10 may have a built-in mechanism for coupling the pressure device 10 to a range of structures in a patient's room.

In some embodiments, a pressure device (not shown) may include a canister composed of a rigid material. In some embodiments, the canister may have as its mouth portion, an adapter inlet, such as that described with reference to FIGS. 1 and 2. In some embodiments, the canister may have an adapter inlet positioned at any location of the canister such that the adapter inlet may be above the highest level of liquid to be provided in the canister.

Accordingly, the canister may be substantially enclosed on all sides except for the adapter inlet. The adapter inlet may be sized to snugly receive and retain an adapter disposed to snugly receive and retain a substantially immovable conduit. The indicia may be provided on the canister in a vertical and descending order from a top portion of the canister to a bottom portion of the canister as described with reference to FIG. 1.

In various embodiments, the pressure device 10 may have one or more of any of the components and/or subsystems described with reference to FIG. 1 or 2.

Figure 3:
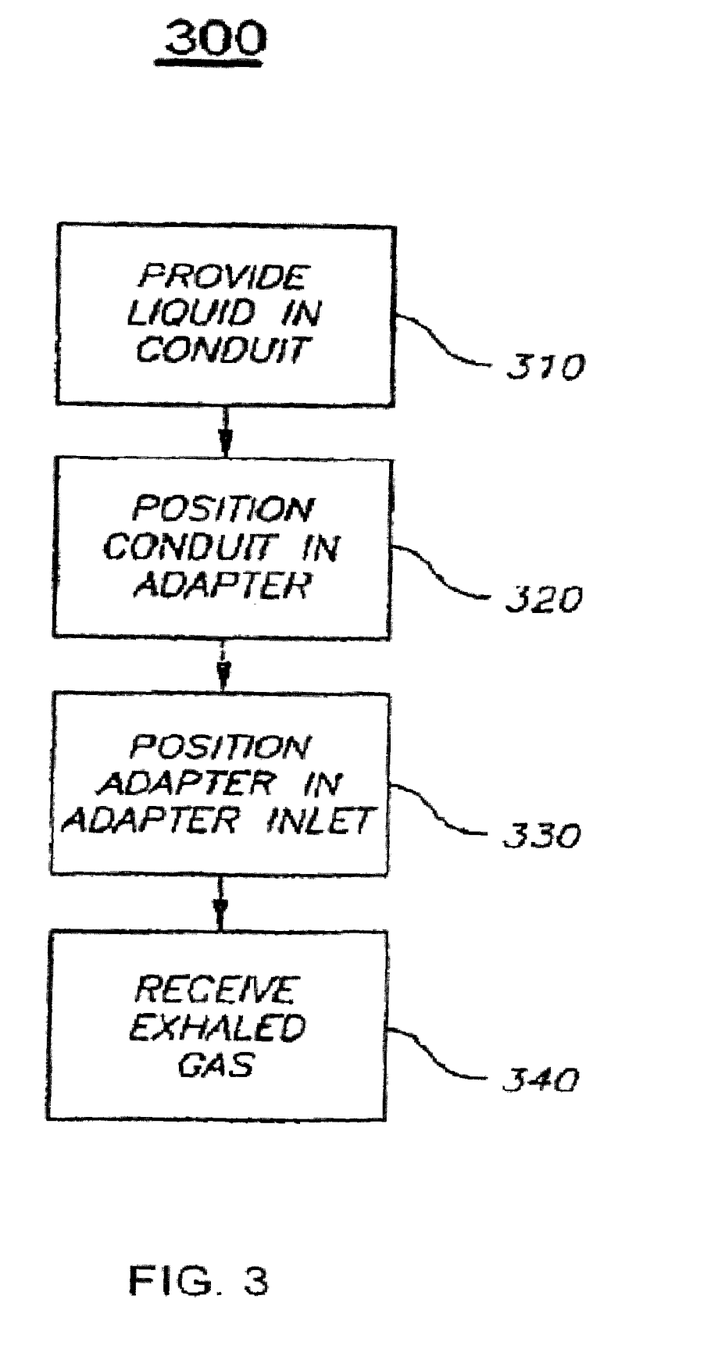
FIG. 3 is a flowchart of a method of operating the pressure device of FIG. 1 according to an embodiment of the present invention.

FIG. 3 is a flowchart of a method of operating the pressure device of FIG. 1 according to an embodiment of the present invention. With reference to FIGS. 1, 2 and 3, the method 300 may include steps 310, 320, 330 and/or 340. In step 310, liquid 17 may be provided in the conduit 50. In step 320, the conduit 50 may be positioned in the adapter 42. In step 330, the adapter 42 may be positioned in the adapter inlet 32. In step 340, exhaled gas may be received.

In some embodiments, the method 300 may also include a step (not shown), wherein gases associated with the liquid in the canister may be filtered and/or a step (not shown), wherein proximal pressure near the respiratory body cavity of a patient may be measured.

Referring again to FIG. 4, in various embodiments a system 400 may include a gas source 410, a humidifier 420, an inspiratory tube 430, a thermometer 440, a respiratory breathing aid 450, an expiratory tube 460 and/or a pressure device 470. In embodiments, the pressure device 470 may be any embodiment of the pressure device 10 described with reference to FIGS. 1, 2 and/or 3.

In some embodiments, the system 400 may also include a pressure release system (not shown) having a spring-loaded pressure release valve in fluid communication with an audible apparatus adapted to generate a sound when the pressure release valve opens. The pressure release valve may be adapted to open when gas output by the gas source 410 may exceed an activation pressure of the pressure release valve. The audible apparatus may be a whistle or a horn and, in some embodiments, may be integrally formed with the pressure release valve. Accordingly, the pressure release system may be used to detect whether gas provided in the inspiratory tube 430 to the patient has exceeded a gas pressure, relieve any received excess gas pressure by opening the pressure release valve and alert a caregiver to any excess pressure by generating a sound.

In some embodiments, the system 400 may also include a universal component adapter (not shown) having a plurality of connectors with one or more different internal diameters ("I.D.s") and/or outer diameters ("O.D.s"). The connectors may be variously configured to provide female and/or male couplings to components in the system.

In some embodiments, the system also includes a proximal airway monitoring conduit 490 and a pressure gauge 495. In some embodiments, the respiratory breathing aid 450 may includes one or more of nasal prongs, a face mask and/or a medical device adapted to be inserted into a patient's nose and/or mouth. In some embodiments, the nasal prongs may be inserted less than one inch into the patient's nose.

The gas source 410 may be coupled to a humidifier 420, which may be coupled to an inspiratory tube 430. The inspiratory tube 430 may be coupled to a thermometer 440, which may be coupled to a respiratory breathing aid 450. The respiratory breathing aid 450 may be coupled to an expiratory tube 460, which may be coupled to a pressure device 470. The proximal airway monitoring conduit 490 may be coupled to the respiratory breathing aid 450 also.

In some embodiments, the gas source 410 may include one or more of an oxygen flowmeter and/or a gas blender. The oxygen flowmeter may output gas to the inspiratory tube 430 at rates of 1-15 liters per minute (lpm). Such rates may result in a build-up of back pressure in the expiratory tube 460 near the location of the patient and the total pressure to the patient may exceed the pressure indicated by the level of the liquid 17 in the canister 20. Accordingly, measurement of proximal airway pressure may be used to verify that the level of the liquid 17 correctly indicates the level of airway pressure experienced by the patient. In some embodiments, a pressure release system (not shown) may be coupled inline with the proximal airway pressure conduit 490 to detect and relieve excess gas pressure and/or to alert a caregiver to the detection of excess gas pressure.

With reference to FIGS. 1 and 4, in some embodiments, the pressure gauge 84 may be coupled to the proximal airway monitoring conduit 490 that may be coupled to expiratory tube 460. In some embodiments, the pressure gauge 84 and the proximal airway monitoring conduit 490 may form a seal that may be substantially airtight. In some embodiments, the pressure gauge 84 may be coupled inline with the proximal airway pressure conduit 490 to detect excess gas pressure.

Additional embodiments of the pressure device will now be described. In some embodiments, the pressure device may be any device having a rigid cap configured to receive exhalatory gas via a conduit that is adjustable in height to provide different airway pressures to the patient. The conduit may be adjustable to any height along a continuum of values from a value corresponding to a maximum pressure value to a value corresponding to a minimum pressure value. In some embodiments, the conduit of the pressure device is slidably adjustable. Accordingly, in various embodiments, the accuracy of the airway pressure that the patient experience may therefore be substantially as high as the accuracy by which a caregiver can adjust the conduit.

In some embodiments, the pressure device may be any device having a rigid cap configured to receive exhalatory gas via a conduit that is adjustable in height to provide different airway pressures to the patient, and having a pre-filled canister of liquid coupled to the cap. The conduit may be adjustable to any height along a continuum of values from a value corresponding to a maximum pressure value to a value corresponding to a minimum pressure value. In some embodiments, the conduit of the pressure device is slidably adjustable. Accordingly, in various embodiments, the accuracy of the airway pressure that the patient experience may therefore be substantially as high as the accuracy by which a caregiver can adjust the conduit. Further, the pre-filled canister may represent a closed system that may reduce infection relative to embodiments wherein the lid of the canister must be removed and/or the level of liquid is adjusted.

In either embodiment, the airway pressure may correspond to any value along the continuum of values. By way of example, but not limitation, the airway pressure may be adjusted to correspond to a first value, may be re-adjusted to correspond to a second value, and may be again re-adjusted to correspond to a third value. The third value may be any intermediate value between the first value and the second value. Accordingly, in various embodiments, the airway pressure may correspond to any value on the continuum, including values that are intermediate to other values. FIGS. 5, 6, 7, 8 and/or 9 are illustrations of one or more embodiments of a pressure device 500 and/or a cap 510, 510 of a pressure device 500 having one or more of these characteristics.

Figure 5:
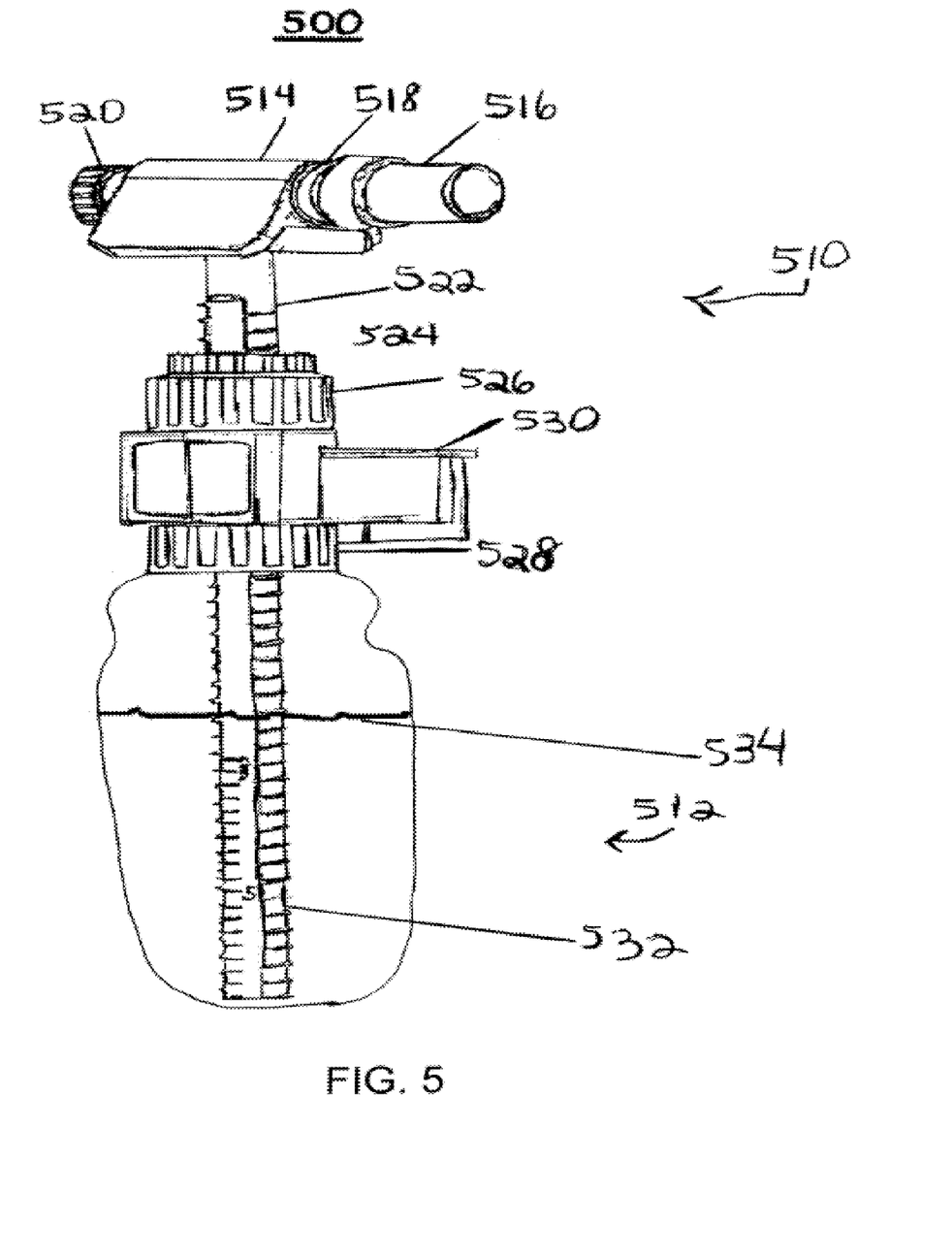
FIG. 5 is a perspective view of a pressure device according to another embodiment of the present invention.
Figure 6:
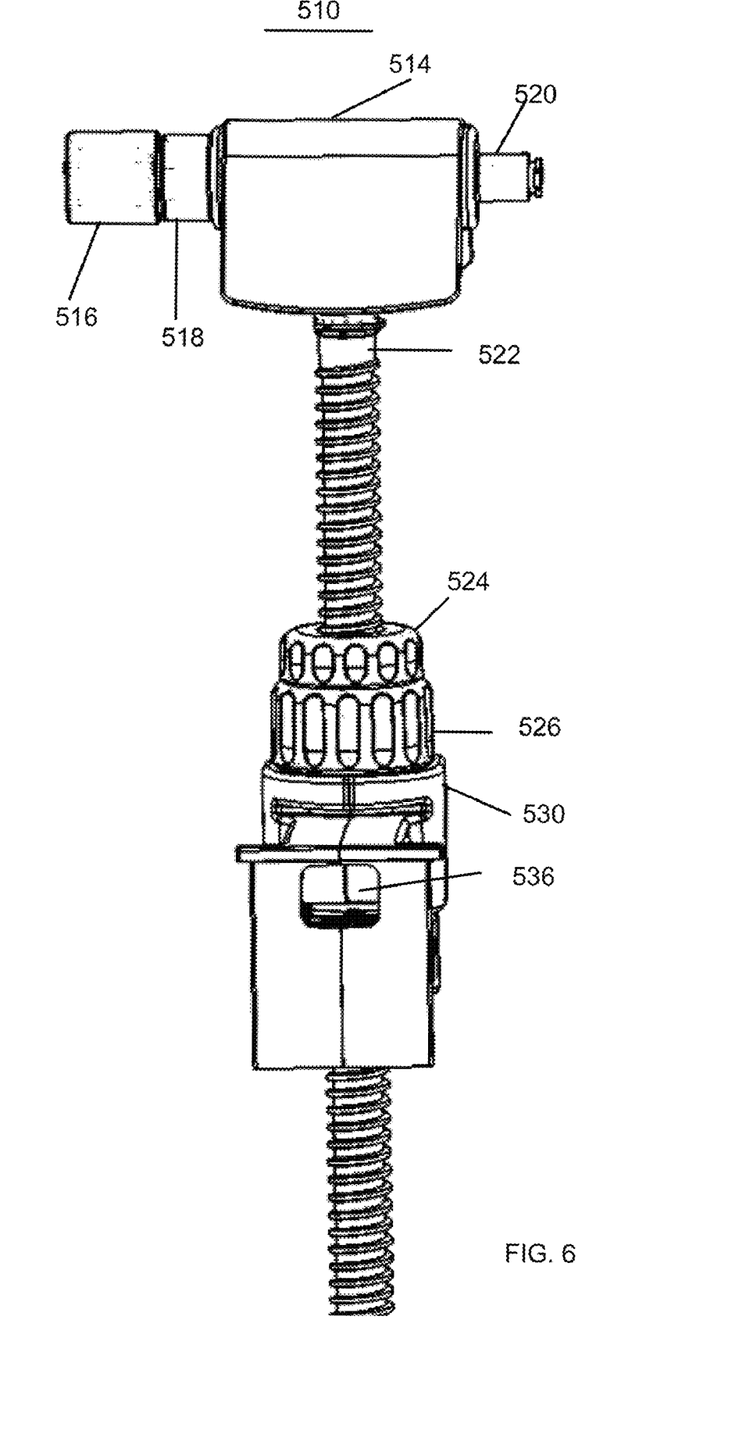
FIG. 6 is a back view of a cap of the pressure device of FIG. 5 according to an embodiment of the present invention.
Figure 7:
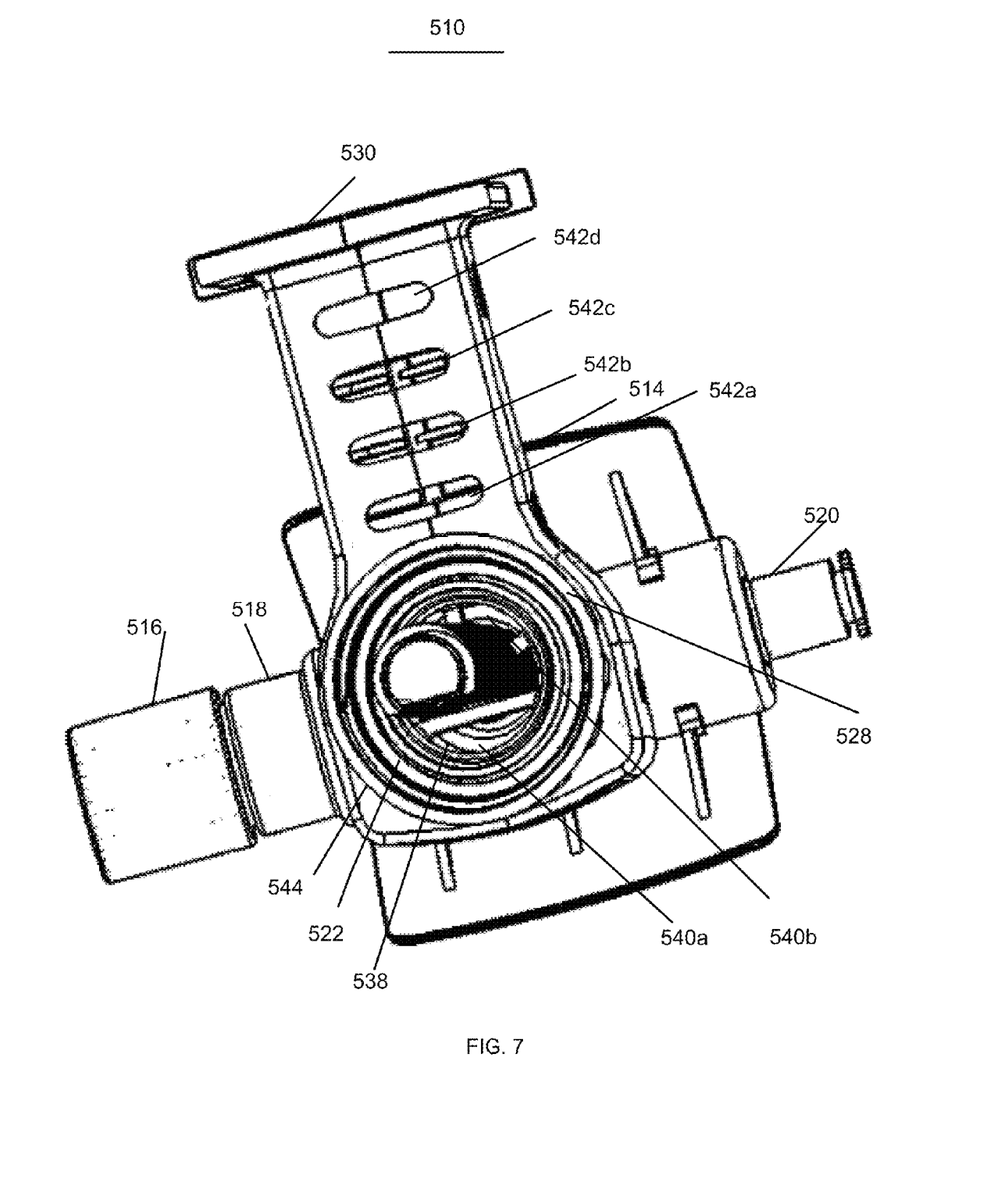
FIG. 7 is a perspective view of the cap of FIG. 6 according to an embodiment of the present invention.
Figure 8:
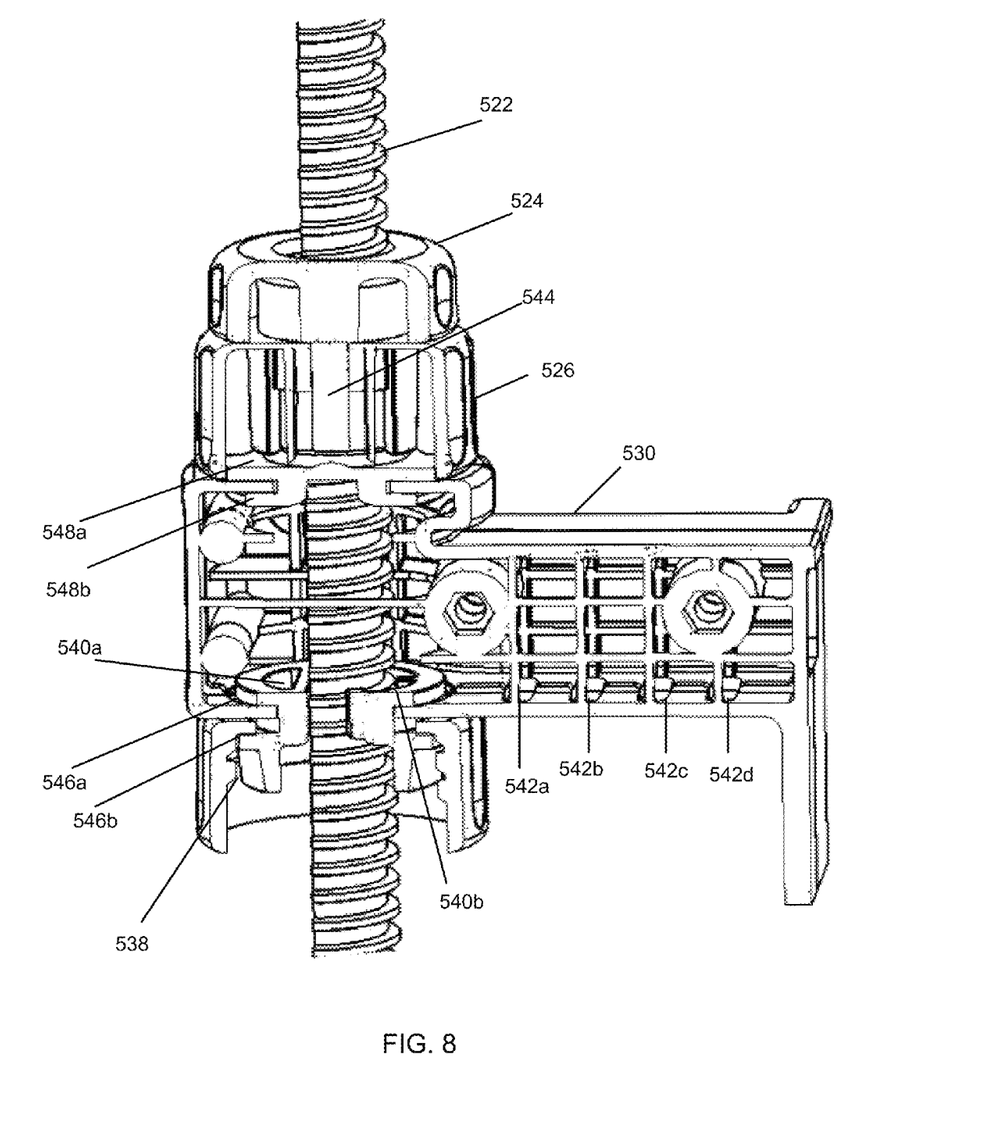
FIG. 8 is a cross-sectional view of the cap of FIG. 6 according to an embodiment of the present invention.
Figure 9:
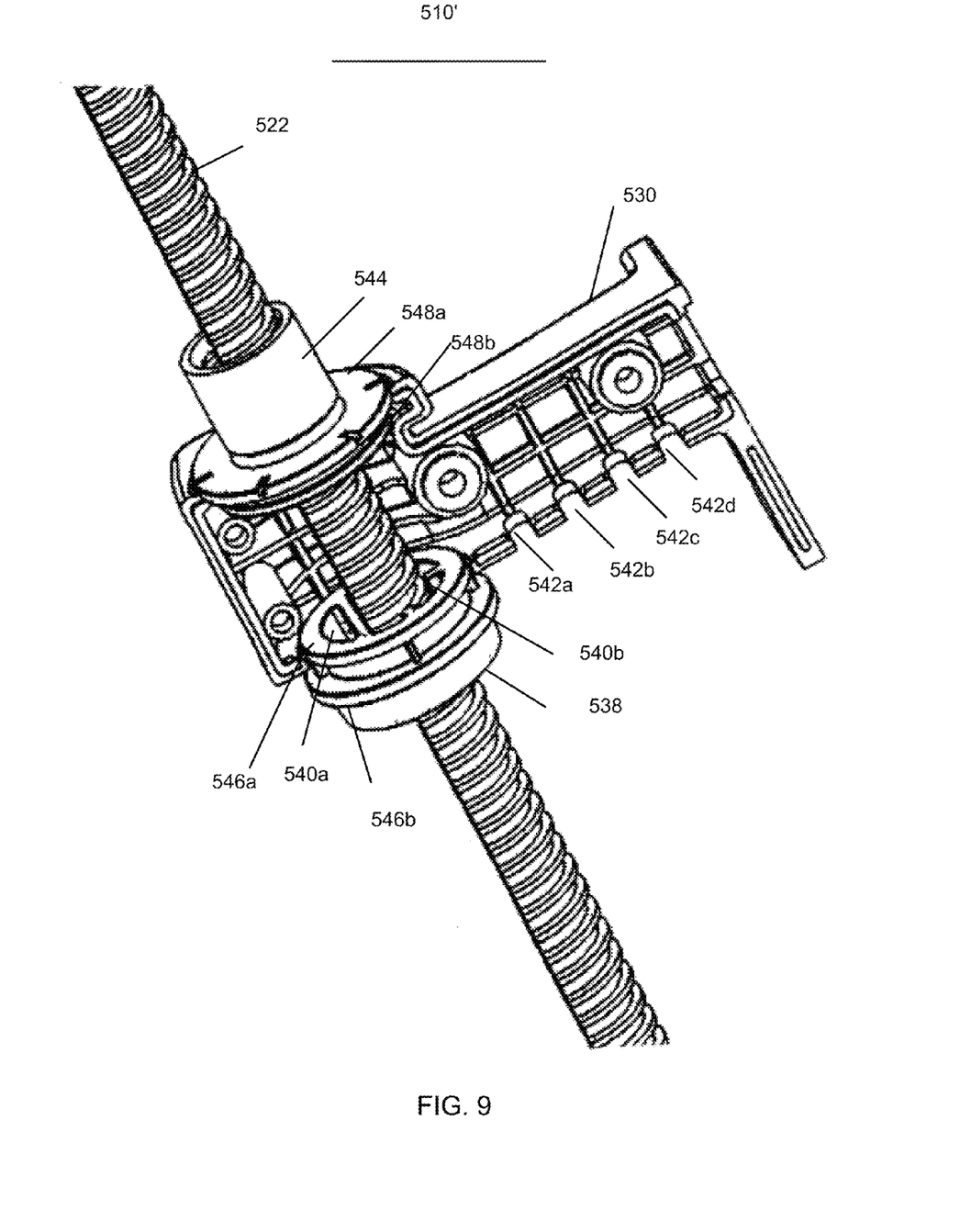
FIG. 9 is a cross-sectional view of a cap of FIG. 6 according to another embodiment of the present invention.

FIG. 5 is a perspective view of a pressure device according to an embodiment of the present invention. FIG. 6 is a back view of a cap of the pressure device of FIG. 5 according to an embodiment of the present invention. FIG. 7 is a perspective view of the cap of FIG. 6 according to an embodiment of the present invention. Embodiments of the invention may include a pressure device and/or a cap of the pressure device. FIG. 8 is a cross-sectional view of the cap of FIG. 6 according to an embodiment of the present invention. FIG. 9 is a cross-sectional view of a cap of FIG. 6 according to another embodiment of the present invention.

The pressure device 500 may include a canister 512 adapted to hold liquid 534 and a cap 510. In some embodiments, the pressure device 500 may include substantially rigid components and/or be less than one pound in weight.

The canister 512 may be a pre-filled bottle of liquid 534 in various embodiments. By way of example, but not limitation, the canister 512 may be a canister of sterile water and/or sterile acetic acid sold by a third-party supplier. In some embodiments, the liquid 534 and/or the canister 512 may not be sold in a sterile form. In some embodiments, the canister 512 may be a 1000 milliliter (ml) bottle pre-filled with 1000 ml of solution. The solution may be water, acetic acid and/or vinegar.

With reference to FIGS. 5, 6, 7, 8 and/or 9, the cap 510 may include a head 514 having an expiratory tube port 516 and a swivel joint 518. The cap 510 may also include a conduit 522, a lock nut 524, an adjust knob 526, an adjust collar 544, a canister connector 528, a cap retainer 538 and/or a bracket 530. In some embodiments, the head 514 of the cap 510 may also include a bleed valve 520. In various embodiments, one or more of the aforementioned components may be disposable or reusable.

The head 514 may include the expiratory tube port 516 coupled to the swivel joint 518. The swivel joint 518 may improve ease of expiratory tube insertion and management, positioning of the head 514 to display labels on the head 514 and/or to display other information regarding the change dates and/or usage of the pressure device 500 and/or the positioning of the canister 512 angle. The swivel joint 518 may provide swivelable movement for the expiratory tube port 516.

The expiratory tube port 516 may have a diameter of 10 mm or 15 mm for easy connection to standard tubing and/or adapters in the BNCPAP circuit. By way of example, and reference to FIG. 4, the expiratory tube port 516 may be coupleable to the expiratory tube 460 such that exhalatory gases from the patient may be provided into the head 514 via the expiratory tube 460 and the expiratory tube port 516. The expiratory tube port 516 may therefore be adapted to swivel in a plurality of directions to accommodate the orientation of an expiratory tube 430 that may be coupled to the expiratory tube port 516.

In some embodiments, the head 514 may be sealed on an end of the head 514 distal from the end on which the expiratory tube port 516 is located. Accordingly, in these embodiments, substantially all exhalatory gas received in the expiratory tube port 516 may be provided to the conduit 522. In some embodiments, the head 514 may be coupled to a bleed valve 520.

The conduit 522 may be tubular and include screw ridges on the exterior surface of the conduit 522. In some embodiments, the conduit 522 may be D-shaped tubular. In some embodiments, the screw ridges are square threads. In some embodiments, the conduit 522 may include approximately 2.36 threads per cm (i.e., approximately 6 threads per inch). In various embodiments, the conduit 522 may include indicia 532 thereon. The indicia 532 may be indicative of an airway pressure through which a patient must exhale. In various embodiments, the caregiver may set and/or adjust the airway pressure by turning the adjust knob 526 (which causes the conduit 522 to move up or down, depending on the direction of rotation of the adjust knob 526), until the indicia 532 of the airway pressure on the conduit 522 is level with the liquid 534.

The airway pressure may be adjusted from 0 cm $H_2O$ to 10 cm $H_2O$. In some embodiments, the indicia 532 may be provided in 0.5 cm increments. In various embodiments, there may be a major marker at each centimeter and a minor tick marker for each 0.5 centimeters. Accordingly, when 2 cm $H_2O$ on the conduit 522 is at water level, the airway pressure is 2 cm $H_2O$. In some embodiments, the second end of the conduit 522 may be set to initially provide an airway pressure value corresponding to an indicia value of 5 or 6 cm. The accuracy of the scale shall be +/−5%.

In some embodiments, six rotations of the adjust knob 526 may result in one inch of movement of the conduit 522. In some embodiments, the conduit 522 may move approximately 0.422 cm for each complete rotation of the adjustment knob 526 (i.e., approximately 0.166 inches for each complete rotation of the adjustment knob 526).

The conduit 522 may be adapted such that the second end of the conduit 522, which may be distal from the first end, may be substantially immovable in a horizontal direction when the pressure device 500 (or cap 510, 510') is in use. The pressure device 500 (or cap 510, 510') may be in use when exhalatory gas is received in the conduit 522 and the conduit 522 is placed in liquid 534 of the canister 512.

The lock nut 524, adjust knob 526, adjust collar 544, canister connector 528 and cap retainer 538 may circumscribe the conduit 522. The lock nut 524 may be adjacent and the adjust knob 526 and the adjust knob 526 may enclose the adjust collar 544. The canister connector 528 may be adjacent the adjust knob 526 and may enclose the cap retainer 538.

In some embodiments, the adjust knob 526 may be removably and/or operably coupled to the adjust collar 544. The adjust collar 544 may include an upper lip 548a and a lower lip 548b with a recess therebetween. The upper lip 548a and the lower lip 548b may be positioned such that the recess between the two lips forms an area dimensioned to snugly retain the top portion of the bracket 530.

The adjust collar 544 may be disposed substantially within the adjust knob 526. In some embodiments, the adjust knob 526 may be operably coupled to the adjust collar 544 such that rotation of the adjust knob 526 causes the underlying adjust collar 544 to rotate.

In some embodiments, the adjust collar 544 may include an interior surface having screw ridges thereon. The conduit 522 may include complementary screw threads such that the screw threads may mate with the screw ridges such that the conduit 522 may move up or down when the adjust collar 544 is rotated. Accordingly, because the screw operation is a continuous movement of the adjust collar 544 along the length of the conduit 522, the airway pressure corresponding to the height of the conduit 522 may be any value along a continuum, including any intermediate values between other values. The number of values that the airway pressure may take on may be substantially infinite in some embodiments, between the height of the conduit 522 corresponding to the maximum airway pressure value and the height of the conduit 522 corresponding to the minimum airway pressure value. Accordingly, in various embodiments, the accuracy of the airway pressure through which a patient must exhale may be limited only by the accuracy by which a caregiver can adjust the conduit 522. Additionally, the caregiver may be able to adjust the height of the conduit 522 using a single hand because the caregiver need only rotate the adjust knob 526.

The lock nut 524 may be adjacent the adjust knob 526 and may include screw threads that are also complementary to the conduit 522 such that the screw threads of the lock nut 524 may mate with the screw threads of the conduit 522. The lock nut 524 may be screwed toward or away from the adjust knob 526 based on the direction of rotation of the lock nut 524. In some embodiments, the lock nut 524 may be rotated in a direction to move the lock nut 524 toward the adjust knob 526 to tighten the lock nut 524 against the adjust knob 526. Accordingly, after the conduit 522 has been adjusted in height by rotating the adjust knob 526, the lock nut 524 may be screwed down onto the adjust knob 526 to further stabilize the height of the conduit 522. This may result in a decreased likelihood that the conduit 522 may move up or down, and that the resultant potentially dangerous change in pressure may result.

The canister connector 528 may be tubular with a top portion and a bottom portion being substantially a top opening and a bottom opening, respectively. The top opening may have a diameter sized to receive and retain the cap retainer 538 and the bottom opening may have a diameter sized to receive and retain the mouth of the canister 512.

In some embodiments, the canister connector 528 may be removably and/or operably coupled to the cap retainer 538, which may provide a coupling between the canister connector 528 and the bottom portion of the bracket 530. In some embodiments, the canister connector 528 may screw down onto a mouth of the canister 512 thereby fastening the cap 510 to the canister 512. In one embodiment, the canister 512 may include 1000 ml acetic acid. By way of example, but not limitation, the canister 512 may be a B Braun PN 0264-2101-0 product or equivalent.

The cap retainer 538 may include an upper lip 546a and a lower lip 546b and a recess therebetween such that the cap retainer 538 retains the canister connector 528 and the bracket 530. The canister 512, which may be fixedly coupled to the canister connector 528, may be rotated to view a label and/or other aspect of the canister 512 thereby improving patient care. stopped here In some embodiments, the cap retainer 538 may include a plurality of apertures 540a, 540b adapted to provide fluid communication between the gases that may reside in the canister 512 and the bracket 530. Accordingly, gas, and corresponding pressure that may build up in the canister 512 may be released through the apertures 540a, 540b.

In some embodiments, the apertures 540a, 540b may have a combined area of approximately 1 inch. In various embodiments, the apertures 540a, 540b may be any shape that may snugly retain the conduit 522. In some embodiments when the conduit 522 is D-shaped, aperture 540a and 540b may be substantially D-shaped and/or any number of other shapes that are dimensioned to snugly retain the conduit 522.

The bracket 530 may include a plurality of bracket gas release apertures 542a, 542b, 542c, 542d in fluid communication with the apertures 540a, 540b such that gas received in the apertures 540a, 540b may be emitted to the environment outside of the cap 510 via the bracket gas release apertures 542a, 542b, 542, 542d. The bracket may also include an attachment aperture 536 adapted to couple to an attachment for coupling the bracket 530 to a support structure (not shown). By way of example, but not limitation, the attachment aperture 536 may be adapted to couple to a clamp disposed to couple to a pole, rail and/or any other structure able to support the cap 510, 510' and/or pressure device 500. In some embodiments, the clamp may be a swivelable clamp able to be swiveled to various orientations to allow the cap 510, 510' and/or pressure device 500 to be clamped to the structure while being maintained in a substantially upright orientation.

In embodiments, the bracket 530 may be adapted such that it may withstand a weight load of approximately 7.5 pounds weight load.

While embodiments of the present invention have been described in connection with exemplary embodiments, it may be to be understood that the invention may be not limited to the disclosed embodiments, but, on the contrary, may be intended to cover various modifications and equivalent arrangements included within the spirit and scope of the specification, appended claims and their equivalents.

What is claimed is:

1. An adjustable airway pressure system comprising: a cap including: a substantially hollow conduit having indicia indicative of a plurality of airway pressure values and being adapted to receive and output exhaled gas, the conduit also having a first plurality of screw threads on an exterior surface of the conduit; and an adjust collar circumscribing the conduit and having an interior surface with a second plurality of screw threads, the second plurality of screw threads coupling and being complementary to the first plurality of screw threads such that a rotation of the adjust collar causes the conduit to move in a substantially vertical direction, the conduit adapted to be adjusted to one of a plurality of heights along a continuum from a first height corresponding to a maximum value of the plurality of airway pressure values to a second height corresponding to a minimum value of the plurality of airway pressure values; an adjust knob circumscribing and coupled to the adjust collar such that the adjust collar is rotated upon rotation of the adjust knob; a cap retainer; a canister connector; and a bracket, the cap retainer retaining the conduit and coupling the canister connector and the bracket; and a canister containing liquid and receiving the conduit such that the received exhaled gas is output from the conduit into the liquid.

2. The adjustable airway pressure system of claim 1, wherein the canister is a pre-filled bottle of water.

3. The adjustable airway pressure system of claim 1, wherein the bracket is in fluid communication with the cap retainer, and the cap retainer includes a first plurality of apertures adapted to emit a volume of the exhaled gas from the canister to the bracket, and the bracket includes a second plurality of apertures adapted to emit the volume of the exhaled gas from the adjustable airway pressure system.

4. The adjustable airway pressure system of claim 1, wherein the cap further comprises a lock nut having a third plurality of screw ridges coupling and complementary to the first plurality of screw threads of the conduit such that a rotation of the lock nut moves the lock nut in a substantially vertical direction along the conduit.

5. The adjustable airway pressure system of claim 4, wherein the lock nut is adapted to fix the adjust knob in a selected position to substantially prevent movement of the conduit.

6. An adjustable airway pressure system cap comprising: a substantially hollow conduit having indicia indicative of a plurality of airway pressure values and being adapted to receive and output exhaled gas, the conduit also having a first plurality of screw threads on an exterior surface of the conduit; and an adjust collar circumscribing the conduit and having an interior surface with a second plurality of screw threads, the second plurality of screw threads coupling and being complementary to the first plurality of screw threads such that a rotation of the adjust collar causes the conduit to move in a substantially vertical direction, the conduit adapted to be adjusted to one of a plurality of heights along a continuum from a first height corresponding to a maximum value of the plurality of airway pressure values to a second height corresponding to a minimum value of the plurality of airway pressure values; an adjust knob circumscribing and coupled to the adjust collar such that the adjust collar is rotated upon rotation of the adjust knob; a cap retainer; a canister connector; and a bracket, the cap retainer retaining the conduit and coupling the canister connector and the bracket.

7. The adjustable airway pressure system cap of claim 6, wherein the bracket is in fluid communication with the cap retainer, and the cap retainer includes a first plurality of apertures adapted to emit a volume of the exhaled gas to the bracket, and the bracket includes a second plurality of apertures adapted to emit the volume of the exhaled gas from the adjustable airway pressure system cap.

8. The adjustable airway pressure system cap of claim 7, further comprising a lock nut having a third plurality of screw ridges coupling and complementary to the first plurality of screw threads of the conduit such that a rotation of the lock nut moves the lock nut in a substantially vertical direction along the conduit.

9. The adjustable airway pressure system cap of claim 8, wherein the lock nut is adapted to fix the adjust knob in a selected position to substantially prevent movement of the conduit.

10. The adjustable airway pressure system cap of claim 7, wherein the bracket is adapted to couple to a swivelable clamp for coupling the adjustable airway pressure system cap to a support structure.

11. The adjustable airway pressure system cap of claim 6, further comprising an expiratory tube port adapted to couple to an expiratory tube in a bubble nasal continuous airway pressure system.

12. A bubble nasal continuous airway pressure system comprising: a gas source adapted to output inspiratory gas; an inspiratory tube adapted to receive the inspiratory gas and provide it to a patient; an expiratory tube adapted to receive the exhaled gas from the patient; and an adjustable airway pressure system having: a cap including: a head coupled to an expiratory tube port for coupling to an expiratory tube and receiving exhaled gas; a substantially hollow conduit having indicia indicative of a plurality of airway pressure values and being adapted to receive and output the exhaled gas from the head, the conduit also having a first plurality of screw threads on an exterior surface of the conduit; and an adjust collar circumscribing the conduit and having an interior surface with a second plurality of screw threads, the second plurality of screw threads coupling and being complementary to the first plurality of screw threads such that a rotation of the adjust collar causes the conduit to move in a substantially vertical direction, the conduit adapted to be adjusted to one of a plurality of heights along a continuum from a first height corresponding to a maximum value of the plurality of airway pressure values to a second height corresponding to a minimum value of the plurality of airway pressure values; an adjust knob circumscribing and coupled to the adjust collar such that the adjust collar is rotated upon rotation of the adjust knob; a cap retainer; a canister connector; and a bracket, the cap retainer retaining the conduit and coupling the canister connector and the bracket; and a canister containing liquid and receiving the conduit such that the received exhaled gas is output from the conduit into the liquid, thereby providing an airway pressure to the patient.

* * * * *